United States Patent [19]

Fisher et al.

[11] 4,162,267

[45] Jul. 24, 1979

[54] PRODUCTION OF CYCLOHEXANONE

[75] Inventors: William B. Fisher; Jan F. Van Peppen, both of Chester, Va.

[73] Assignee: Allied Chemical Corporation, Morris Township, Morris County, N.J.

[21] Appl. No.: 918,134

[22] Filed: Jun. 22, 1978

[51] Int. Cl.² .................... C07C 27/00; C07C 29/20; C07C 45/00

[52] U.S. Cl. ................................ 260/586 P; 568/835

[58] Field of Search ..................... 260/586 P; 568/835

[56] References Cited

U.S. PATENT DOCUMENTS

| | | | |
|---|---|---|---|
| 2,692,240 | 10/1954 | Sprauer ............................... | 252/412 |
| 2,760,940 | 8/1956 | Schwarzenbek ...................... | 252/466 |
| 2,777,805 | 1/1957 | Lefrancois et al. ................... | 196/50 |
| 2,829,166 | 4/1958 | Joris et al. .......................... | 260/586 P |
| 2,857,337 | 10/1958 | Hamilton et al. ..................... | 252/472 |
| 2,857,432 | 10/1958 | Joris .................................. | 260/586 P |
| 2,873,296 | 2/1959 | Nilsson et al. ....................... | 260/586 P |
| 3,076,810 | 2/1963 | Duggan et al. ...................... | 260/586 P |
| 3,187,050 | 6/1965 | Duggan et al. ...................... | 260/582 |
| 3,305,586 | 2/1967 | Phielix ............................... | 260/586 P |
| 3,542,863 | 11/1970 | Zimmerschied ...................... | 260/525 |
| 3,692,845 | 9/1972 | Cheema et al. ..................... | 260/621 A |
| 3,959,382 | 5/1976 | Yeh et al. ........................... | 260/586 P |
| 3,965,187 | 6/1976 | Little et al. ........................ | 260/586 P |

FOREIGN PATENT DOCUMENTS

| | | |
|---|---|---|
| 892562 | 2/1972 | Canada. |
| 2163362 | 7/1972 | Fed. Rep. of Germany. |
| 2357370 | 5/1974 | Fed. Rep. of Germany. |
| 2619660 | 11/1976 | Fed. Rep. of Germany. |

*Primary Examiner*—Norman Morgenstern
*Attorney, Agent, or Firm*—Fred L. Kelly; Richard A. Anderson

[57] ABSTRACT

A controlled process for preparation of cyclohexanone by liquid phase, catalytic hydrogenation of phenol in two or more hydrogenation stages by correlating a predetermined mole ratio of phenol to cyclohexanone with a predetermined maximum temperature in each of the hydrogenation stages, whereby intrinsic safety of operation is achieved by operating at temperatures at or below the atmospheric boiling point in each reactor. The process provided improved control by use of a hydrogenation gas comprising hydrogen and nitrogen and recycling unreacted gas to the reaction zone to promote flashing overhead of product cyclohexanone. At least part of the recycling gas is treated by a cryogenic hydrogen recovery process to remove inerts from the system.

10 Claims, No Drawings

PRODUCTION OF CYCLOHEXANONE

CROSS-REFERENCES TO RELATED APPLICATIONS

This application is related to U.S. Applications
Ser. No. 527,466 filed Nov. 26, 1974;
Ser. No. 667,760 filed Mar. 17, 1976;
Ser. No. 667,735 filed Mar. 17, 1976;
Ser. No. 793,563 filed May 4, 1977; U.S. Pat. No. 4,092,360,
Ser. No. 827,189 filed Aug. 23, 1977;
Ser. No. 853,720 filed Nov. 21, 1977; and
Ser. No. 886,719 filed Mar. 15, 1978.

BACKGROUND OF THE INVENTION

This invention relates to the hydrogenation of phenol and, more particularly, to the control of the hydrogenation of phenol to cyclohexanone in the presence of a promoted palladium catalyst.

In the hydrogenation of phenol employing a palladium catalyst, the activity of the catalyst, and hence the rate of hydrogenation, decreases with continued use of the catalyst due to impurities present in the hydrogenation reaction mixture which poison the catalyst. While processes, such as those disclosed in U.S. Pat. Nos. 3,692,845 and 3,187,050, have been developed to purify organic compounds such as phenol to be hydrogenated, the poisoning of metallic catalysts has not been entirely eliminated in large scale commercial processes due to long-term accumulation of impurities, such as those impurities which are introduced with the phenol and the hydrogen gas, and those impurities which are produced during the processing.

To avoid the economically prohibitive alternatives of discarding poisoned catalyst or continuing to use the poisoned catalyst at a reduced rate of hydrogenation, it is desirable to promote the rate of hydrogenation, thereby overcoming the disadvantages of continued use of such poisoned palladium catalysts. The hydrogenation of phenol to cyclohexanone has been promoted by the use of "promoted palladium-on-carbon catalysts", i.e., catalysts which have been treated prior to their addition to the hydrogenation reaction mixture, to incorporate on the catalysts a material which enhances their activity. Thus, in U.S. Pat. No. 3,076,810, cyclohexanone is produced by hydrogenating phenol using a sodium-promoted catalyst, i.e., a palladium catalyst which has been modified prior to its introduction to the reactive mixture, to incorporate sodium thereon. Alkaline reacting agents in limited amounts are also disclosed as being added to assist in promotion when the sodium-promoted catalysts of that reference are employed. However, such catalyst systems have not been entirely satisfactory, and research has continued to develop an improved process and/or catalyst.

Following the Flixborough, England disaster in 1974, which resulted in loss of lives and equipment destruction, the inherent danger involved in synthesis of cyclohexanone using high temperature, liquid phase processes became clearly evident, i.e., the potential formation and detonation of organic vapor clouds was fully recognized and defined:

(a) Leakage of process vapor has proved to be a problem that may be solved within the constraints of existing technology; it requires vapor detection devices and combative actions, such as automated unit isolation, system shutdown, or water fog vapor suppression.

(b) Cataclysmic rupture of liquid lines and vessels containing volumes of organic liquids above the atmospheric boiling point has proved to be a very serious problem within the constraints of existing technology. Intrinsic safety requires operating temperatures to be at or below atmospheric boiling point of the reaction mixture in each vessel. However, in known processes, such lower operating temperatures greatly reduce production capacity.

U.S. application Ser. No. 886,718 filed Mar. 15, 1978, relates to a highly active catalyst for selective hydrogenation of phenol to cyclohexanone. The catalyst comprises 0.2 to 10 weight percent of palladium, based on the total weight of the catalyst, supported on carbon particles having diameters of 3 to 300 microns and a surface area of 100 to 2000 $m^2$/gram, said catalyst being promoted by sodium in an amount of at least 1000 ppm. Preferably, said sodium-promoted palladium catalyst is additionally promoted during said hydrogenation by contacting the catalyst with phenol containing a small amount of an in situ promoter selected from the group consisting of sodium hydroxide, sodium carbonate, and sodium phenate, said amount being 10 to 300 ppm in terms of sodium of said in situ promoter.

The highly active catalyst of U.S. application Ser. No. 886,718 is an important contribution to this art because it permits hydrogenation of phenol with reduced amounts of catalyst and with intrinsic safety by operating at temperatures at or below the atmospheric boiling point of the reaction mass. However, we have found that control of the hydrogenation reaction is difficult with use of the highly active catalyst, and research has been continued to develop an improved method for controlling the process.

SUMMARY OF THE INVENTION

According to the present invention, we provide a controlled process for preparation of cyclohexanone by liquid phase, catalytic hydrogenation of phenol in 2 to 8 hydrogenation stages by using a sodium-promoted palladium-on-carbon catalyst at a temperature of 135° C. to 184° C. and correlating a predetermined mole ratio of phenol to cyclohexanone with a predetermined maximum temperature in each of the hydrogenation stages, intrinsic safety of operation being achieved by operating at temperatures at or below the atmospheric boiling point in each reactor. The process provides improved control by use of a hydrogenation gas comprising hydrogen and nitrogen under superatmospheric pressure and recycling unreacted gas to the reaction zone to promote flashing overhead of product cyclohexanone. At least part of the recycling gas is treated by a cryogenic hydrogen recovery process to remove inerts from the system.

DESCRIPTION OF THE PREFERRED EMBODIMENT

The preferred process of the present invention may be briefly stated as follows: A controlled process for producing cyclohexanone by liquid phase hydrogenation of phenol in the presence of a sodium-promoted palladium-on-carbon catalyst at a temperature of 145° C. to 184° C., said catalyst being further characterized in that it is composed of palladium coated carbon particles, said carbon particles having diameters of 3 to 300 microns and a surface area of 100 to 2000 $m^2$/gram, said phenol containing 11 to 150 ppm sodium in the form of an in situ promoter selected from the group consisting of sodium hydroxide, sodium carbonate, sodium phenate and mixtures thereof, said hydrogenation reaction being carried out in a reaction zone comprising 2 to 8 reactors, in series arrangement, wherein the mole ratio of phenol to cyclohexanone in each reactor and the reaction temperature in each reactor are correlated so that the reaction temperature approaches but does not exceed the atmospheric boiling point of the reaction mixture in each reactor, said hydrogenation reaction being controlled in part by adjusting the hydrogen pressure in the reactors, said process being further controlled by: (a) reacting said phenol with a hydrogenation gas comprising nitrogen and hydrogen, and also including methane and argon as contaminants, at superatmospheric pressure, and recycling unreacted gas to the reaction zone;

(b) cooling at least part of the gas being recycled to subambient temperature, desirably 0° to 15° C., to thereby partially condense it and form a condensate phase containing cyclohexanone and a gaseous phase containing hydrogen, nitrogen, methane and argon, and separating the phases;

(c) passing the gaseous phase containing hydrogen, nitrogen, methane and argon through an absorbent bed, preferably activated carbon, to extract any residual cyclohexanone therefrom;

(d) then cooling the gaseous phase containing hydrogen, nitrogen, methane and argon to cryogenic temperature to partially condense it and form a condensate phase containing nitrogen, argon and methane and a hydrogen-enriched gaseous phase containing nitrogen and argon, and separating the phases; and (f) recycling said gaseous hydrogen-enriched phase to the reaction zone to adjust the partial pressure of hydrogen therein and promote flashing overhead of cyclohexanone produced in the reaction.

Desirably, the gas containing hydrogen, nitrogen methane and argon from step (c) of the above-described process is passed through a conventional molecular sieve to extract any water that may be present in the gas, before the gas is cooled to cryogenic temperature in step (d) of the process.

The palladium catalysts useful in the present invention contain palladium in either its elemental or combined form, as a catalytically active metal. Preferably, 30 to 75 percent or more of the total palladium is present as elemental palladium, i.e., as palladium zero. The palladium is desirably absorbed or coated on the surface of a support consisting of carbon particles, said carbon particles having diameters of 3 to 300 microns and a surface area of 100 to 2000 m$^2$/gram. It is preferred that the catalyst have about 95 to 98 weight percent of the particles between 4 and 150 microns in diameter. While the amount of palladium incorporated on the selected support may vary widely, the catalyst preferably contains from about 0.2 to 10 weight percent palladium. A satisfactory and readily prepared catalyst contains 1 to 5 weight percent palladium on charcoal. In addition, the palladium catalysts useful in the present invention may contain catalytically active metals in addition to palladium. Such additional catalytically active metals which may be employed are those selected from the group consisting of elements of the platinum series. Exemplary of platinum series elements which may be employed are ruthenium, rhodium, osmium, iridium, platinum and mixtures thereof.

The in situ promoters of the present invention are members selected from the group consisting of sodium hydroxide, sodium carbonate, sodium phenate, and mixtures thereof. Particularly preferred as in situ promoters in the present invention are sodium hydroxide and sodium phenate, with sodium phenate being especially preferred. The selected promoter may be added to the hydrogenation reaction mixture as a phenol slurry containing up to about 25 weight percent, and preferably from about 1 to 10 weight percent, of the selected promoter. Alternatively, the promoter may be added to the hydrogenation reaction mixture as an aqueous solution.

Although in U.S. Pat. No. 3,076,810 it was said that higher concentrations, i.e., more than 10 ppm, of an alkaline reacting compound in the phenol favored the formation of undesirable cyclohexanol, we have found that in the presence of our improved palladium-on-carbon catalyst, not only is the reaction rate enhanced but also the production of cyclohexanol is reduced by operating within the range of 10 to 300 ppm of alkali metal in the phenol. The reason for this surprising improvement is not known with certainty, but it is believed that the unexpected element involves the apparent interaction of the in situ promoter with the catalyst, together with careful control of the reaction conditions as specified hereinabove.

The phenol which may be employed in the present invention may be obtained from conventional sources, such as by the oxidation of cumene to form cumene hydroperoxide and the decomposition of the resulting hydroperoxide. However, the phenol treated in accordance with the process of the present invention will generally contain no more than about 100 ppm sulfur impurities, and preferably not greater than about 10 ppm sulfur impurities containing divalent sulfur, not greater than about 20 ppm sulfur impurities containing tetravalent sulfur and not greater than about 80 ppm, and most preferably not greater than about 40 ppm, sulfur impurities containing hexavalent sulfur.

The phenol also preferably contains not greater than 2 ppm, and most preferably not greater than 1 ppm, iron values (calculated as elemental iron); and preferably not greater than 100 ppm, and most preferably not greater than 50 ppm, acetol (i.e., hydroxy-2-propanone).

The phenol hydrogenated in accordance with the process of the present invention may also contain a wide variety of other impurities. These impurities include, for example, halogen compounds and deleterious nitrogen compounds, i.e., nitrogen-containing compounds which inhibit the hydrogenation of phenol to cyclohexanone employing palladium catalysts. Typical deleterious nitrogen compounds include aromatic amines, ammonium salts, polyamines, and tertiary and primary amines. Preferably, the phenol contains less than 10 ppm halogen and less than 50 ppm of nitrogen as deleterious nitrogen compounds.

The selected promoter may be introduced to the hydrogenation reaction mixture either prior to hydrogenation or during hydrogenation. Thus, the conditions of temperature under which the promoter may be added to the hydrogenation mixture are not critical and may vary widely. For example, the temperature at which the promoter is added to the hydrogenation reaction mixture may vary from about 25° C. to about 185° C. and the pressure may vary from about atmospheric to 300 psig. While an improved rate of hydrogenation is generally observed immediately upon addition to the hydrogenation reaction mixture of a promoter of the present invention, even more improved results may be obtained where the hydrogenation reaction mixture is maintained at a temperature within the range of about 135° C. to 184° C., preferably 145° C. to 184° C., for a period of 15 to 30 minutes after addition thereto of the selected promoter.

The selected in situ promoter may be added to the hydrogenation reaction mixture either continuously or batchwise. Upon withdrawal of the hydrogenation product from the reaction zone, the palladium catalyst may be recovered from the product stream and returned to the zone for hydrogenation of additional phenol. The recovery of the catalyst from the product stream may be effected by any standard solids separation procedure, e.g., centrifugation, vacuum filtering, and the like.

Vessels which may be employed during the hydrogenation are conventional, and include typical hydrogenation apparatus such as, for example, the apparatus described in U.S. Pat. No. 3,076,810. Also, cryogenic hydrogen recovery plants are well known. For example, Petrocarbon Developments Limited, Manchester, England, has developed cryogenic plants suitable for recovering hydrogen from various waste gas streams.

In one preferred embodiment of the present invention, 3 to 5 reactors are connected in series arrangement for hydrogenation of the phenol to cyclohexanone. Each reactor has adjustable means for adjusting the hydrogenation feed rate and setting the hydrogen pressure therein, whereby the rate of hydrogenation in each reactor can be controlled. A portion of the cyclohexanone formed in each reactor is taken overhead as vapor, condensed, and separated. For convenience, this vaporized portion of the cyclohexanone may be called "cyclohexanone flash". Preferably, at least 50 percent of the cyclohexanone formed in the process is vaporized from the reaction mixture as cyclohexanone flash. The maximum reaction temperature in each reactor is limited for reasons of safety based on the mole ratio of phenol to cyclohexanone in the reaction mixture. Table 1 indicates the preferred maximum reaction temperature for various mole ratios of phenol to cyclohexanone in the reaction mixture.

TABLE 1

| Reaction Mole Ratio of Phenol to Cyclohexanone | Maximum Reaction Temperature, °C. |
|---|---|
| 90/10 | 182.0 |
| 80/20 | 184.0 |
| 70/30 | 184.0 |
| 60/40 | 181.0 |
| 50/50 | 177.0 |
| 40/60 | 172.5 |
| 30/70 | 168.0 |
| 20/80 | 164.0 |
| 10/90 | 159.0 |
| 5/95 | 158.0 |

It will be seen from Table 1 that higher reaction temperatures can be maintained with intrinsic safety when a relatively large amount of product cyclohexanone is vaporized from the reaction mixture to thereby increase the mole ratio of phenol to cyclohexanone in the reaction mixture. To this end, the present process features use of a hydrogenation gas comprising hydrogen and nitrogen and recycling unreacted gas to the reaction zone to promote flashing overhead of product cyclohexanone. At least part of the recycling gas is treated by a cryogenic hydrogen recovery method to remove excess nitrogen and other inerts from the system and prevent the concentration of these impurities in the reaction zone from exceeding an acceptable level. Without said removal of excess inerts from the system, they accumulate unduly in the reaction zone as time proceeds, thereby lowering the partial pressure of the reacting hydrogen and hence reducing cyclohexanone yield. Normally, sufficient nitrogen is maintained in the recycling gas to provide a hydrogenation gas comprising hydrogen and nitrogen in a ratio of about 2 to 3 parts of hydrogen to 1 part of nitrogen, by volume. The hydrogen content of the hydrogenation gas is readily controlled by increasing or decreasing the proportion of recycling gas being fed to the cryogenic hydrogen recovery procedure.

The present invention is further illustrated by reference to the following examples wherein parts and percentages are by weight unless otherwise indicated.

EXAMPLE 1

This example demonstrates the advantages of the improved process of the present invention.

The first of a series of five agitated hydrogenation vessels is charged with 55,000 parts per hour of phenol, 2.0 parts per hour of sodium hydroxide, and 1,200 parts per hour of a sodium-promoted, palladium-on-carbon catalyst having a sodium content of 0.5 percent, said catalyst containing about 0.9 percent palladium on carbon particles having diameters of about 5 to 150 microns and a surface area of about 1,000 $m^2$/gram. About 67 percent of the palladium on the catalyst is present as elemental palladium. Each hydrogenation vessel is connected in series so that the reaction mixture flows through the five vessels in about 3.1 hours, the hydrogen being charged to the first vessel.

The hydrogen is charged as a hydrogenation gas comprising hydrogen and nitrogen together with recycled unreacted gas which has been treated by a cryogenic hydrogen recovery process to remove impurities as described hereinafter. As charged, the total hydrogenation gas contains 2,639 parts per hour hydrogen, 11,677 parts per hour nitrogen, 235 parts per hour argon and 209 parts per hour methane. In accordance with the present invention, preferably about 25 to 30 percent excess hydrogen over the stoichiometric requirement is charged based on the phenol consumed in the process. The reaction pressure is between 100 and 230 psig. Reaction temperature is 176° C. in the first vessel; 170° C. in the second vessel; 167° C. in the third vessel; 163° C. in the fourth vessel; and 158° C. in the fifth vessel. The reaction mixture in the fifth vessel, primarily cyclohexanone, contains 8 percent phenol which may be recovered and recycled in the process. It is noteworthy for reasons of safety that the temperature in each vessel is below the atmospheric boiling point of the reaction mixture present in the vessel.

About 33,000 parts per hour of distillate, primarily cyclohexanone, is separated from the five vessels; this distillate is rectified to provide substantially pure cyclohexanone. The reaction mass flowing from the fifth reaction vessel is fed to a continuous centrifuge, wherein the catalyst is separated from the crude cyclohexanone; the catalyst is recycled in the process. The crude cyclohexanone is rectified to recover substantially pure cyclohexanone which may be combined with the cyclohexanone recovered as described above. The unreacted hydrogenation gas is treated by a multistep cryogenic hydrogen recovery procedure and recycled to the reaction zone as described below.

The unreacted hydrogenation gas flowing from the fifth reaction vessel contains about 556 parts per hour hydrogen, 11,677 parts per hour nitrogen, 235 parts per hour argon, 209 parts per hour methane, and 38 parts per hour cyclohexanone. This unreacted hydrogenation gas is compressed to 395 psig. and cooled to 5° C. to condense and separate about 32 parts per hour of cyclohexanone. The residual cyclohexanone is removed from the gas, together with small amounts of other organic compounds, by passing the gas through a bed of activated carbon. Desirably, the resulting purified gas is then passed through a conventional molecular sieve to remove any water that may be present, which would otherwise solidify in the cryogenic section.

The cryogenic section consists of a series of heat exchangers mounted within a "cold box", in which the dry, cyclohexanone-free unreacted hydrogenation gas is cooled and partially condensed to give a hydrogen-enriched gaseous phase containing nitrogen and argon and a methane-enriched liquid phase containing nitrogen and argon. The gaseous and liquid phases are separated and returned through the heat exchangers, thereby giving up their refrigeration in cooling the incoming feed. The hydrogen-enriched gaseous stream is then available, at ambient temperature and at a pressure of about 310 psig. for recycling in the process, i.e., for direct entry to any one or more of the hydrogenation vessels to increase flashing of product cyclohexanone from the reaction mixture and thereby control the phenol-cyclohexanone mole ratio, or for mixing with hydrogenation gas being charged to the first of the series of five hydrogenation vessels. This hydrogen-enriched gaseous stream contains about 545 parts per hour hydrogen, 2,406 parts per hour nitrogen, and 66 parts per hour argon. The methane-enriched stream containing about 11 parts per hour hydrogen, 9,268 parts per hour nitrogen, 169 parts per hour argon and 209 parts per hour methane is purged from the process.

In this continuous operation carried out for several days, cyclohexanone recovery is 51,250 parts per hour. Also recovered is 824 parts per hour of cyclohexanol, 1,782 parts per hour of phenol, and 254 parts per hour of higher boiling by-products. Only 2 parts per hour of makeup catalyst is required in the process. Similar results are obtained when an equivalent amount of sodium as sodium carbonate or sodium phenate is substituted for the sodium hydroxide added to the process in the phenol.

EXAMPLE 2

The procedure of Example 1 is followed except that about 10 percent of the unreacted hydrogenation gas flowing from the fifth reaction vessel is not treated by the multistep cryogenic hydrogen recovery procedure of Example 1, but instead is compressed to 395 psig. and recycled to any one or more of the hydrogenation vessels, thereby increasing flashing of product cyclohexanone from the reaction mixture to improve the control of the phenol to cyclohexanone mole ratio of the reaction mixture. It will be seen from Table 1 that higher reaction temperatures can be maintained with intrinsic safety when a relatively large amount of cyclohexanone is vaporized from the reaction mixture to thereby increase the mole ratio of phenol to cyclohexanone therein.

DISCUSSION

The complex interaction of the process variables in this multi-stage, co-current flash product removal reactor system, with phenol, catalyst and vent gas recycle streams, provides a formidable challenge both in process optimization and in development of a precise and reliable control system. Therefore, the disclosed operating conditions and choice of control parameters are not obvious, even to professionals familiar with the art.

We claim:

1. A controlled process for preparation of cyclohexanone by liquid phase, catalytic hydrogenation of phenol in 2 to 8 hydrogenation stages by using a sodium-promoted palladium-on-carbon catalyst at a temperature of 135° C. to 184° C. and correlating a predetermined mole ratio of phenol to cyclohexanone with a predetermined maximum temperature in each of the hydrogenation stages, whereby intrinsic safety of operation is achieved by operating at temperatures at or below the atmospheric boiling point in each reactor, said process being further characterized by use of a hydrogenation gas comprising hydrogen and nitrogen and recycling unreacted gas to the reaction to promote flashing overhead of product cyclohexanone, at least part of the unreacted gas being cooled to cryogenic temperatures prior to recycling to remove excess inerts from the system.

2. The process of claim 1 wherein the phenol contains a small amount of an in situ promoter selected from the group consisting of sodium hydroxide, sodium carbonate, and sodium phenate.

3. The process of claim 2 wherein said in situ promoter contained in said phenol is sodium hydroxide.

4. The process of claim 2 wherein said in situ promoter contained in said phenol is sodium carbonate.

5. The process of claim 2 wherein said in situ promoter contained in said phenol is sodium phenate.

6. The process of claim 2 wherein the phenol is hydrogenated at a temperature of 145° C. to 184° C.

7. The process of claim 2 wherein the palladium is coated on carbon particles having diameters of 3 to 300 microns.

8. The process of claim 2 wherein the amount of in situ promoter in said phenol is 11 to 150 ppm in terms of sodium of said in situ promoter.

9. The process of claim 2 wherein 30 to 75 percent of the total palladium is elemental palladium.

10. A controlled process for producing cyclohexanone by liquid phase hydrogenation of phenol in the presence of a sodium-promoted palladium-on-carbon catalyst at a temperature of 145° C. to 184° C., said catalyst being further characterized in that it is composed of palladium coated carbon particles, said carbon particles having diameters of 3 to 300 microns and a surface area of 100 to 2,000 m$^2$/gram, said phenol containing 11 to 150 ppm sodium in the form of an in situ promoter selected from the group consisting of sodium hydroxide, sodium carbonate, sodium phenate and mixtures thereof, said hydrogenation reaction being carried out in a reaction zone comprising 2 to 8 reactors, in series arrangement, wherein the mole ratio of phenol to cyclohexanone in each reactor and the reaction temperature in each reactor are correlated so that the reaction temperature approaches but does not exceed the atmospheric boiling point of the reaction mixture in each reactor, said hydrogenation reaction being controlled in part by adjusting the hydrogen pressure in the reactors, said process being further controlled by:

(a) reacting said phenol with a hydrogenation gas comprising nitrogen and hydrogen, and also including methane and argon as contaminants, at superatmospheric pressure, and recycling unreacted gas to the reaction zone;

(b) cooling at least part of the gas being recycled to subambient temperature to thereby partially condense it and form a condensate phase containing cyclohexanone and a gaseous phase containing hydrogen, nitrogen, methane and argon, and separating the phases;

(c) passing the gaseous phase containing hydrogen, nitrogen, methane and argon through an absorbent bed, comprising activated carbon, to extract any residual cyclohexanone from said gaseous phase;

(d) then cooling the gaseous phase containing hydrogen, nitrogen, methane and argon to cryogenic temperature to partially condense it and form a condensate phase containing nitrogen, argon and methane and a hydrogen-enriched gaseous phase containing nitrogen and argon, and separating the phases; and (e) recycling said gaseous hydrogen-enriched phase to the reaction zone to adjust the partial pressure of hydrogen therein and promote flashing overhead of cyclohexanone produced in the reaction.

* * * * *